United States Patent [19]

Rosen

[11] 4,130,567

[45] Dec. 19, 1978

[54] PROCESS FOR THE PREPARATION OF ARYL DIOXOLANES

[75] Inventor: George Rosen, Wayne, N.J.

[73] Assignee: Sun Chemical Corporation, New York, N.Y.

[21] Appl. No.: 834,961

[22] Filed: Sep. 20, 1977

[51] Int. Cl.$^2$ .......................................... C07D 317/26
[52] U.S. Cl. ............................................. 260/340.9 R
[58] Field of Search .................................. 260/340.9 R

[56] References Cited

U.S. PATENT DOCUMENTS

| | | | |
|---|---|---|---|
| 3,344,148 | 9/1967 | Dietrich | 260/340.9 R |
| 3,526,641 | 9/1970 | Wesslen et al. | 260/340.7 |

*Primary Examiner*—Ethel G. Love
*Attorney, Agent, or Firm*—Cynthia Berlow

[57] ABSTRACT

This invention relates to a process for preparing aryl dioxolanes.

6 Claims, No Drawings

PROCESS FOR THE PREPARATION OF ARYL DIOXOLANES

Aryl dioxolanes are known, as is their use as herbicides (disclosed in U.S. Pat. No. 3,344,148) and as photosensitizers (disclosed in U.S. Pat. No. 3,607,693). As taught in the art, 4-phenyl-4-benzoyldioxolane is prepared by reacting benzoin with formaldehyde in the presence of an entraining agent to facilitate the removal of evolved water, as illustrated by the equation

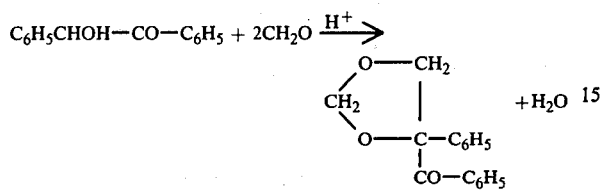

As usually run under reflux at atmospheric pressure, the formaldehyde vaporizes and reforms as paraformaldehyde in the reactor head space.

This method has many disadvantages. In the first place, a large excess of formaldehyde is required in order to maintain the correct stoichiometry. Furthermore, the paraformaldehyde frequently blocks the reactor, preventing the completion of the reaction and necessitating the expenditure of considerable time and effort to remove the paraformaldehyde from the overhead. When the reaction is not completed, i.e., the benzoin is not completely converted, purification of the product 4-benzoyl-4-phenyldioxolane (BPD) is difficult because benzoin has limited solubility in the usual solvents. Thus, before use the BPD must be recrystallized, and even then some benzoin remains. This is not acceptable, because benzoin causes gelation in some photocurable formulations. When, for example, the BPD, prepared by this process and recrystallized, was to be used as a photoinitiator in a coating composition, the amount of residual benzoin was sufficient to cause the composition to gel during storage.

These disadvantages have been overcome and sufficiently pure 4-benzoyl-4-phenyldioxolane prepared in high yield by the process of this invention whereby the reaction of benzoin with formaldehyde in the presence of a catalyst is carried out under pressure in a sealed reactor.

Although this invention will be described by the reaction of formaldehyde with benzoin, it is not intended to be limited thereto. The process of this invention is equally applicable to the reaction of formaldehyde with a variety of compounds having the general formula

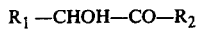

which upon reaction with 2CH$_2$O gives the product

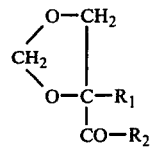

wherein $R_1$ and $R_2$ is each an aromatic or a heteroaromatic group which may be substituted with one or more hydroxy, halogen, lower alkyl, aryl, alkaryl, cycloalkyl, nitro, etc., groups, and $R_1$ and $R_2$ may be the same or different. Typical starting compounds include, but are not limited to, benzoin; furoin; anisoin; p-chlorobenzoin; p'-chlorobenzoin; p,p'-dichlorobenzoin; o-hydroxybenzoin; p,p'-dicyclohexylbenzoin; m-phenylbenzoin; m-tolylbenzoin; m,m'-dinitrobenzoin; and the like.

In general in this process the formaldehyde is used in the form of paraformaldehyde; it is, however, within the scope of this invention to use formaldehyde in any other convenient form, such as trioxane.

The present process requires less excess of paraformaldehyde to preserve stoichiometry than does the process run with azeotropic water removal at atmospheric pressure. In addition, it eliminates the need for cleaning paraformaldehyde from the reactor head space, condenser, etc.; it simplifies the work-up procedure; and it produces a product that is sufficiently pure to be used without recrystallization.

In general, with paraformaldehyde as a reactant the reaction temperature is about 120 to 200, and preferably about 130° to 170° C.; with trioxane it is generally about 100 to 150, and preferably about 110° to 130° C.

The pressure, a function of the reaction temperature and the ratio of formaldehyde to benzoin, is autogenous.

The molar ratio of formaldehyde to benzoin is not critical as long as it is sufficient to ensure a high degree of reaction in a reasonable time; for practical purposes a molar ratio of about 2.2 to 1 has been found suitable.

Any suitable material may be used as the catalyst, such as for example p-toluenesulfonic acid, sulfuric acid, hydrochloric acid, or other material classified as a Bronsted or Lewis acid.

The invention will be further described in the following examples wherein, unless otherwise specified, all parts are by weight.

EXAMPLE 1

(A) A 200-ml. pressure bottle containing a magnetic stirrer was charged with 53.1 ggrams (0.25 mol) of benzoin, 18.2 grams (0.55 mole at 91% purity) of paraformaldehyde, and 1.3 grams of p-toluenesulfonic acid. The bottle was then connected to a vacuum pump and to a nitrogen cylinder via a 2-hole rubber stopper. After alternately evacuating and breaking the vacuum with nitrogen three times, the bottle was sealed and placed into an oil bath on a stir-hot plate. The temperature was raised to 160° C. and the heating continued for 4½ hours. The mixture was then cooled to 70° C. and the bottle opened. Toluene (84 ml.) was added, and the mixture was transferred to a separatory funnel. The lower aqueous layer was removed; the organic solution was then washed successively with 10% sodium hydroxide and 10% sodium chloride, dried, and the solvent removed. The yield was 60 grams (93.2%) of a product that was shown by gas chromatographic analysis to be 98.6 percent BPD and 1.4 percent benzoin.

(B) The product of part (A) was used without further purification as a photoinitiator for isocyanate-modified pentaerythritol triacrylate in a ratio of 5:95; the composition cured in 1.7 seconds when exposed to a source of ultraviolet radiation.

EXAMPLE 2

1062 Grams (5.0 gm-mol) of benzoin, 364 grams (11.0 gm-mol at 91% purity) of paraformaldehyde, and 26 grams of p-toluenesulfonic acid were charged into a 1-gallon stainless steel autoclave. The reactor was flushed with nitrogen, sealed, and heated at 140° ± 3° C. for 3½ hours at a pressure of 60–95 psig. The reactor contents were withdrawn, diluted with 1477 grams of benzene, washed successively with 10% sodium hydroxide and 10% sodium chloride, dried, and the solvent removed. The yield was 953 grams (73.7%) of a product that was shown by gas chromatographic analysis to be 98.2% BPD and the remainder mostly benzoin.

The product was used without further purification as a photoinitiator.

EXAMPLE 3

1062 Grams (5.0 gm-mol) of benzoin, 330 grams (11.0 gm-mol) of trioxane, and 26 grams of p-toluenesulfonic acid were charged into a 1-gallon stainless steel autoclave. The reactor was flushed with nitrogen, sealed, and heated at 115° ± 3° C. for 24 hours at a pressure of 25–32 psig. The reactor contents were withdrawn, diluted with 1207 grams of benzene, washed successively with 10% sodium hydroxide and 10% sodium chloride, dried, and the solvent removed. The yield was 1062 grams (81.3%) of a product that was shown by gas chromatographic analysis to be 97.3% BPD and the remainder benzoin.

The product was used without further purification as a photoinitiator.

EXAMPLE 4

The procedure of Example 2 was repeated with each of the following instead of benzoin: furoin; anisoin, p-chlorobenzoin; o-hydroxybenzoin; p,p'-dicyclohexylbenzoin; m-tolylbenzoin; and m,m'-dinitrobenzoin.

What is claimed is:

1. In the process for preparing a compound having the formula

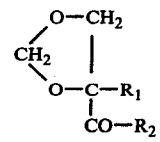

by reacting formaldehyde with a compound having the formula $R_1$—CHOH—CO—$R_2$ wherein $R_1$ and $R_2$ is each an aromatic or a heteroaromatic group which may be substituted with at least one halogen, hydroxy, lower alkyl, aryl, alkaryl, cycloalkyl, or nitro group and $R_1$ and $R_2$ may be the same or different, the improvement which comprises carrying out the reaction under autogenous pressure.

2. The process of claim 1 wherein the formaldehyde is used in the form of paraformaldehyde.

3. The process of claim 1 wherein the formaldehyde is used in the form of trioxane.

4. The process of claim 2 wherein the reaction temperature is about 120° to 200° C.

5. The process of claim 3 wherein the reaction temperature is about 100° to 150° C.

6. The process of claim 1 wherein the starting compound is benzoin; furoin; anisoin; p-chlorobenzoin; p,p'-dichlorobenzoin; o-hydroxybenzoin; p,p'-dicyclohexylbenzoin; m-phenylbenzoin; m-tolylbenzoin; or m,m'-dinitrobenzoin.

* * * * *